(12) United States Patent
Mistrik et al.

(10) Patent No.: US 9,943,331 B2
(45) Date of Patent: Apr. 17, 2018

(54) METHOD OF AN EXTRACTION OF FOLLICULAR CELLS AND A DEVICE FOR PURSUANCE OF THIS METHOD

(71) Applicant: UNIVERZITA PALACKEHO, Olomouc (CZ)

(72) Inventors: Martin Mistrik, Olomouc (CZ); Jiri Bartek, Greve (DK)

(73) Assignee: UNIVERZITA PALACKEHO, Olomouc (CZ)

( * ) Notice: Subject to any disclaimer, the term of this patent is extended or adjusted under 35 U.S.C. 154(b) by 244 days.

(21) Appl. No.: 14/649,785

(22) PCT Filed: Nov. 19, 2013

(86) PCT No.: PCT/CZ2013/000152
§ 371 (c)(1),
(2) Date: Jun. 4, 2015

(87) PCT Pub. No.: WO2014/086324
PCT Pub. Date: Jun. 12, 2014

(65) Prior Publication Data
US 2015/0297253 A1   Oct. 22, 2015

(30) Foreign Application Priority Data
Dec. 4, 2012   (CZ) .............................. PV 2012-871

(51) Int. Cl.
*A61B 17/50*   (2006.01)
*A61B 17/322*   (2006.01)
(Continued)

(52) U.S. Cl.
CPC ............ *A61B 17/322* (2013.01); *A61B 10/02* (2013.01); *A61B 10/0283* (2013.01);
(Continued)

(58) Field of Classification Search
CPC ......... A61B 2017/00752; A61B 2017/320064; A61B 17/3468; A61B 17/32053; A61B 17/322
See application file for complete search history.

(56) References Cited

U.S. PATENT DOCUMENTS

| 4,240,435 A | 12/1980 | Yazawa et al. |
| 5,873,888 A * | 2/1999 | Costanzo ............ A61B 17/3468 606/131 |

(Continued)

FOREIGN PATENT DOCUMENTS

| FR | 2 683 127 A1 | 5/1993 |
| FR | 2 744 624 A1 | 8/1997 |

(Continued)

OTHER PUBLICATIONS

International Search Report (PCT/ISA/210) dated Feb. 21, 2014, by the European Patent Office as the International Searching Authority for International Application No. PCT/CZ2013/000152.

(Continued)

*Primary Examiner* — Tuan V Nguyen
(74) *Attorney, Agent, or Firm* — Buchanan, Ingersoll & Rooney PC

(57) ABSTRACT

A method of an extraction of follicular cells which is based on a principle of a hair extraction from a skin of mammals by the help of an extraction device, when during the extraction remains preserved also the root part of the hair surrounded by follicular cells, where the essence of the invention is that at least one hair from a sampling point of the skin is sucked in by the help of vacuum which is led form a body of the extraction device into an interspace of a two-cone collet fixed partly to the body and partly to an arbor where is subsequently by the interspace closing between its inner cone and an outer cone by the help of a counter pressure of the arbor this hair grasped and after it extracted from the (Continued)

Figure 1:
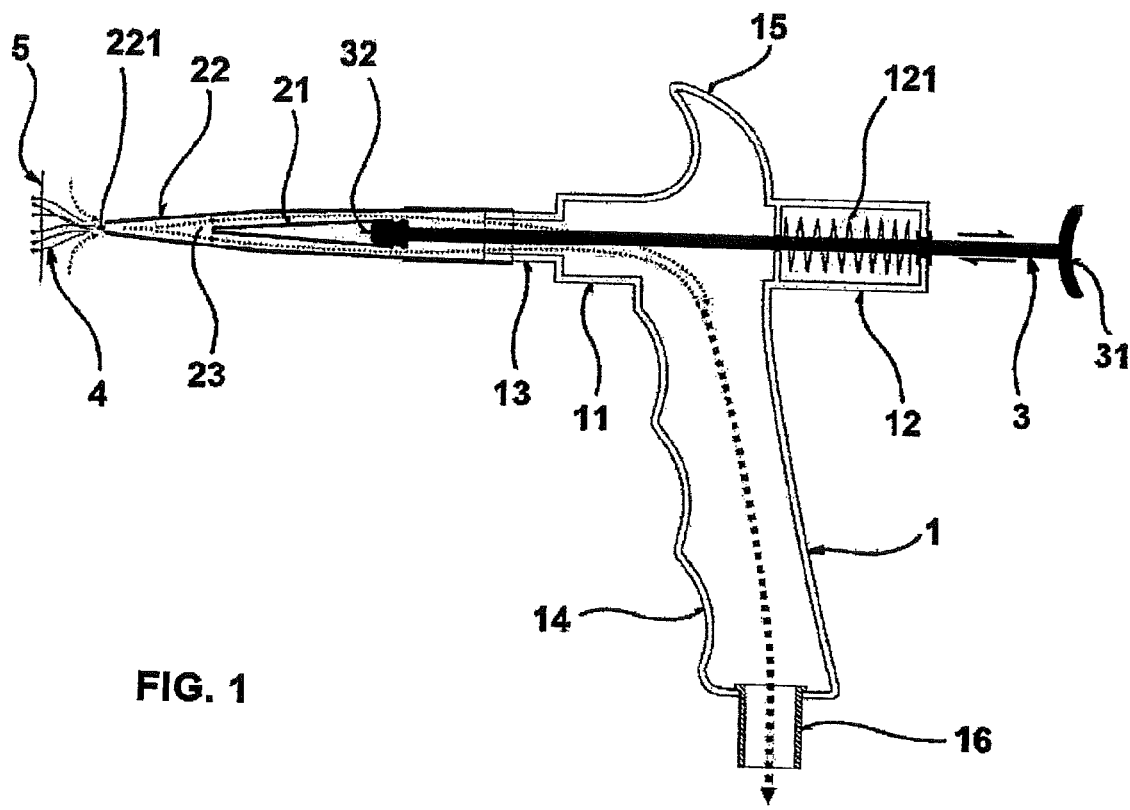

skin. The extracting device for an extraction of follicular cells consists of the hollow two surface collet formed by the inner cone and the outer cone and of the hollow body which is equipped partly with in a forward direction positioned hollow nozzle, partly with a connector for supply of vacuum and partly is in it embedded the sliding arbor whereas in the collet is between the inner cone and the outer cone formed the free interspace when the inner cone of the collet is fixed on the arbor and the outer cone which is equipped with the branch inlet is fixed on the nozzle of the body.

10 Claims, 1 Drawing Sheet

(51) Int. Cl.
    *A61B 10/02*     (2006.01)
    *A61B 17/00*     (2006.01)
    *A61B 17/32*     (2006.01)
(52) U.S. Cl.
    CPC ............... *A61B 2010/0208* (2013.01); *A61B 2017/00424* (2013.01); *A61B 2017/00752* (2013.01); *A61B 2017/3225* (2013.01); *A61B 2017/320064* (2013.01); *A61B 2217/005* (2013.01)

(56) References Cited

U.S. PATENT DOCUMENTS

| | | | |
|---|---|---|---|
| 6,059,807 A | 5/2000 | Boudjema | |
| 2008/0033455 A1* | 2/2008 | Rassman | A61B 17/32053 606/133 |
| 2008/0234602 A1* | 9/2008 | Oostman | A61B 10/0266 600/564 |
| 2009/0005765 A1 | 1/2009 | Oostman, Jr. et al. | |

FOREIGN PATENT DOCUMENTS

| | | |
|---|---|---|
| FR | 2 776 180 A1 | 9/1999 |
| WO | WO 2005/027795 A1 | 3/2005 |
| WO | WO 2010/117043 A1 | 10/2010 |

OTHER PUBLICATIONS

Written Opinion (PCT/ISA/237) dated Feb. 21, 2014, by the European Patent Office as the International Searching Authority for International Application No. PCT/CZ2013/000152.

Czech Republic Search Report for PV 2012-871 dated Jun. 25, 2013.

* cited by examiner

METHOD OF AN EXTRACTION OF FOLLICULAR CELLS AND A DEVICE FOR PURSUANCE OF THIS METHOD

ART DOMAIN

The invention belongs to an area of a biological material extraction used mainly in medicine, forensic and biotechnological laboratories of a basic and applied research and refers to a method of a follicular cells extraction from hair of mammals, especially from a human body, whereas a part of the invention is an extraction device for pursuance of this method.

PRESENT PRIOR ART

A human body vellus is as well as an animal hair a collection of different types of hair which mutually differentiate by its morphology and a position on the body. Follicular cells are cells which proximate surround root of the hair and from which the hair grows. These are the cells with specific characteristics when by the help of different microscopic, chemical and biochemical methods it is possible to obtain a lot of information. Follicular cells are used for example at an alopecia (baldness) studies, during a research of live primary cells with a well-preserved proliferation capacity, during different medicine examinations including a personal biodosimetry when it is possible to examine a chemotherapy efficiency or an activity of negative influences of environment. Follicular cells are likewise used for DNA obtaining for example for forensic, taxonomic or other purposes.

The hair follicles extraction is at present done either by an invasive or a non-invasive way. The invasive way assumes a tissue excision in a proximate surrounding of a hair root and further processing of this way extracted tissue. An invasive operation always means an infection risk, permanent scarring, discomfort and for some types of hair, for example in case of eye lashes or eyebrows, it is a very difficult way applicable method. On the other side the invasive approach is only method successfully used for a hair transplantation and a whole range of specialised devices has been developed for this purpose, and these devices are described for example in the files WO2010117043 A1 and WO2005027795 A1.

Non-invasive methods consist in a hair extraction, including its root part, namely in the way to keep in the area of a hair root as many follicular cells as possible. To reach this it is possible to use different types of hand or electric tweezers, walings or forceps. Such specific tool is described for example in the file US4240435 A1. A disadvantage of classical metal tweezers and forceps used especially for a selective hair removal is a hair rupture risk in the place where the hair is weakened by the grip. Yet from the gain of follicular cells point of view the minimization of the risk of a hair rupture is an important aspect. A further important standpoint is a control of an extraction process itself, which must proceed relatively slowly due to a gradual break away of follicular cells from a skin matrix. Devices known from example from the files KR100895291 B1 and FR2683127 A1 are primary designed for a cosmetic application use where is a general endeavour to carry out an extraction of the hair as fast as possible due to a pain minimization, however these solutions do not generally enable obtaining of a sufficient amount of follicular cells. Last but not least a time consuming factor and a grip easiness of a particular hair into an extraction device, thus hair follicular cells, play an important role during a hair extraction. It is known a whole range of electric devices which are used for a hair extraction. For example in the file US2001051808 A1 there is described a device which works on basis of rotating discs which meet together. Yet this device is also primarily designed for cosmetic purposes for a surface depilation therefore is largely non-selective and above all the hair is after its extraction immediately released and this significantly complicates further manipulation with this biologic material. And it is namely a subsequent manipulation with an extracted hair which is an important aspect for follicular cells processing for experimental needs. If the hair is to be subsequently manipulated it is suitable for it to be held in the device, with which it was extracted. For this purpose several devices in the form of forceps have been developed when the extracted hair is mechanically held in the extraction device. These designs of an extraction device are known for example from the files CN2281764 Y, CN201082171 Y. A disadvantage of mentioned devices is the fact, that they are compact and do not enable for example a separation of an extracting part, which would hold fast the hair itself and at the same time would enable its further manipulation.

The aim of the presented invention is to introduce a brand new non-invasive way of a follicular cells extraction and an extraction device for pursuance of this method, when the hair extraction is carried out based on a principle of a hair grip between two dovetailed cones, which this way create an extraction collet, whereas it is advantageous for an extracted material to be held in the device by which it was extracted. During a hair extraction has to be, due to obtaining of a sufficient amount of follicular cells, minimized risk of a hair rupture in the place where the hair is weakened by the grip. The extraction process itself is possible to carry out also on more hair at the same time, namely in a very short time interval whereby is minimized time necessary for finding, grasping and subsequent extraction of the hair.

Essence of the Invention

The mentioned goal is to a large extend met by a featured invention, which is a method of an extraction of follicular cells based on a principle of a hair removal from a mammals skin by the help of an extraction device, when during an extraction remains preserved also the root part of the hair which is surrounded by follicular cells, where an essence of the invention is fact that at least one hair is sucked in from a skin sampling point by the help of vacuum led from the body of an extraction device into an interspace of a two-cone collet which is fixed partly to the body and partly to an arbor where is subsequently by the interspace closing between its inner cone and an outer cone by the help of an counteracting pressure of the arbor the hair grasped and afterwards extracted from the skin.

It is advantageous when an interspace closing of the collet is applied by a pressure on the arbor on whose head is set the inner cone.

Likewise another essence of the invention is an extraction device for an extraction of follicular cells based on a principle of a hair removal from a mammal skin when during the extraction remains preserved also the root part of the hair which is surrounded by follicular cells, where the extraction device consists of a hollow double surface collet formed by an inner cone and an outer cone and of a hollow body which is partly in the forward direction procured with a hollow nozzle, partly is equipped with a connector for vacuum supply and partly is in it set a sliding arbor, whereas in the collet is between the inner cone and the outer cone formed a free interspace, when the inner cone of the collet is fixed on the arbor and the outer cone which is procured with an inlet branch is fixed on the nozzle of the body.

In an advantageous design the inner cone and the outer cone of the collet are basically shape identical and are telescopically set on the extraction device to allow closing of the interspace of the collet, whereas the inlet branch of the outer cone is through the interspace of the collet and further through the nozzle, an inner cavity and the connector connected to a vacuum source.

Also is advantageous when the body is formed in the shape of a handle, whereas is procured with an opposite way placed front case and a back case where is set the sliding arbor which is two-side led out from the body.

In an optimal design is from the front case of the body led out a hollow conical nozzle in a forward direction and a pressure spring is placed in the back case.

Furthermore is advantageous when the arbor is on its back end procured with a pressure stay and on its front end is equipped with a nozzle.

Likewise is advantageous when the body is from the side of the front wall procured with a shaping for an easy grip for fingers and from the side of the upper wall is equipped with a shaped coracoid stay.

With this invention is reached, in comparison with to date known solutions, a new and higher effect in that, that by the help of a collet, which consists of two dovetailed cones removable fixed on the extraction device is enabled an extraction of a sufficient amount of an organic material. It is easily enabled to grasp a hair between two conical walls of a collet in the way that the pressure of these walls on the hair is divided on an area sufficiently large to minimize hair weakening in the place of grasp. This way grasped hair can be easily extracted from the skin, whereas there is no risk of its rupture and there remains preserved even its root part which is surrounded by follicular cells. The collet is made of a soft, light, inert sterilized material, it is easy for production and at the same time enables further manipulation with an obtained organic material out of the extraction device.

FIGURES CLARIFICATION

Figure 2:
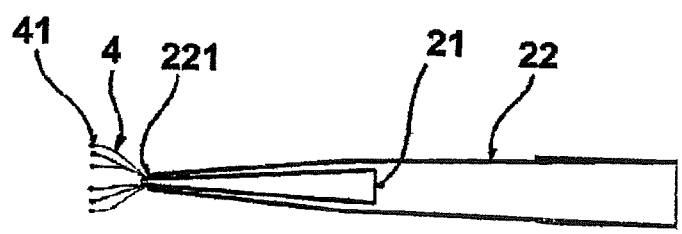

Particular examples of the invention design are simple way illustrated in enclosed drawings where, FIG. 1 is a lengthwise section of an extraction device FIG. 2 is a lengthwise section of a collet with grasped hair The drawings which illustrate featured invention and subsequently described examples of a particular design do not in any case limit protection extend mentioned in the definition yet only clarify the essence of given solution.

EXAMPLES OF THE INVENTION DESIGN

An extraction device illustrated in FIG. 1 is formed by a hollow body 1 in the shape of a handle, which is procured with an opposite way placed front case 11 and a back case 12 in which is set a sliding arbor 3 two side led out from the body 1, whereas from the front case 11 is in the forward direction led out a conical nozzle 13 and in the back case 12 is placed a pressure spring 121. The pressure spring 121 is made and set in the back case 12 in the way that it prevents a spontaneous back push of the arbor 3 and thus also an inner cone 21 of a collet 2 which is fixed on a head 32 of the arbor 3, when there is by the influence of vacuum formed a force acting on the inner cone 21 of the collet 2. A front wall of the body 1 is equipped with a shaping 14 for an easy grip for fingers, an upper wall of the body 1 is equipped with a shaped coracoid stay 15 and in a lower wall of the body 1 is fixed a connector 16 of supply of a non-illustrated vacuum source. The arbor 3 is on its end which stands out from the back case 12 procured with a pressure stay 31 and on its opposite end with a head 32. A second integral part of the extraction device is a two surface collet 2, which consists of two practically shape identical telescopic hollow truncated cones 21, 22 which are preferably made of a soft inert sterilized plastic material and are dimensioned in the way that the inner cone 21 is by its base fixable on the head 32 of the arbor 3 and the outer cone 22 is fixable on an outer surface of the nozzle 13 of the body 1.

During preparation of the extraction device for use it is at first the inner cone 21 of the collet 2 slipped over on the head 32 of the arbor 2 and then is the outer cone 22 of the collet 2 slipped over on the nozzle 13 in the way that between particular cones 21,22 is formed a free interspace 23, wherewith the device is prepared and ready for use. After connection to the vacuum source is through an inlet branch 221 of the outer cone 22 sucked in air into the interspace 23 of the collet 2 and after positioning of the branch inlet 221 to a sampling point of the skin the end parts of one or more hair 4 are sucked in. Afterwards is by the pressure on the stay 31 of the arbor 3 pushed the inner cone 21 of the collet 2 to an inner surface of its outer cone 22, wherewith comes to grasping of sucked in hair 4, which can be then, by a gentle pull of the device, extracted from the skin. The inner cone 21 and the outer cone 22 of the collet 2 have just right conical shape and a material of which are produced, just right softness and elasticity that it comes to locking of the inner cone 21 into the outer cone 22 and at the same time the pressure in the grasping point of the hair 4 is gentle enough not to weaken the structure of the hair 4 and not to rupture the hair 4 during its extraction from the skin 5. The arbor 3 in the back case 12 of the body 1 comes through an inserted pressure spring 121.

As it is schematically illustrated in FIG. 2 by the help of the conical collet 2 the hair 4 is grasped between the outer cone 22 and the inner cone 21 and its root part 41 which is surrounded by follicular cells remains preserved during the extraction. The whole collet 2, or just its part, is suitable for further manipulation including fixation and storing procedures, whereas it enables to mark easily an extracted organic material with a legend or a sticker.

INDUSTRIAL EFFICIENCY

A method of an extraction of follicular cells based on a principle of a hair removal from a mammal skin and an extracting device for pursuance of this method are efficient especially in biotechnological laboratories for a basic and applied research which deal with a research of alopecia, skin diseases, cancer, biodosimetry, forensic techniques and taxonomic classification of mammals.

The invention claimed is:

1. An extraction device for non-invasive extraction of follicular cells by extraction of a hair from the skin of mammals, the extraction device comprising a hollow body, the hollow body comprising a hollow nozzle positioned in a forward direction, with a connector for connecting the extraction device to a vacuum source, and with a sliding arbor, the arbor being disposed in the hollow nozzle, and a hollow double surface collet, the collet comprising an inner cone and an outer cone, and forming an interspace between the inner cone and the outer cone, wherein the inner cone is fixed on the sliding arbor, the outer cone is fixed on the hollow nozzle, and wherein the inner cone and the outer cone are adapted for grasping at least one hair from a sampling point of the skin at an inlet of the outer cone and in the interspace between the inner cone and the outer cone.

2. The extraction device for non-invasive extraction of follicular cells according to the claim 1, wherein the inner cone and the outer cone of the collet are substantially identical in shape and set up telescopically for closing of the collet interspace.

3. The extraction device for non-invasive extraction of follicular cells according to claim 1, wherein the inlet of the outer cone, the interspace of the collet and the hollow nozzle of the body, and an inner cavity of the body are adapted for connection to the vacuum source through the connector.

4. The extraction device for non-invasive extraction of follicular cells according to the claim 1, wherein the hollow body is formed in the shape of a handle, wherein the body is further equipped with a front case, the front case being placed in a forward direction, and with a back case, the back case being placed opposite to the front case, and wherein the sliding arbor is further led out of the hollow body on both sides, and is disposed in the front case and the back case.

5. The extraction device for non-invasive extraction of follicular cells according to the claim 4, wherein the hollow body is led out of the front case of the body in the forward direction, wherein the hollow nozzle has a conical shape, and wherein a pressure spring is placed in the back case.

6. The extraction device for non-invasive extraction of follicular cells according to claim 1, wherein the sliding arbor comprises a pressure stay on a back end of the arbor and a head on a front end of the arbor.

7. The extraction device for a non-invasive extraction of follicular cells according to the claim 1, wherein the inner cone and the outer cone of the collet are further adapted for holding the at least one hair for further manipulation independently on the body of the extraction device.

8. A non-invasive method of extraction of follicular cells by extraction of a hair from a skin of mammals, said method being performed by the extraction device according to claim 1 and comprising the following steps:
    connecting of the extraction device to a vacuum source through the connector,
    positioning of the inlet of the outer cone to a sampling point of a skin,
    sucking of at least one hair from a sampling point of the skin in the inlet of the outer cone of the extraction device,
    closing of the collet interspace formed by the inner cone and the outer cone of the extraction device,
    grasping of the at least one hair at the inlet of the outer cone between the inner cone and the outer cone, and
    extracting the grasped at least one hair from the skin.

9. The method of claim 8 further comprising the steps of
    holding the at least one hair at the inlet of the outer cone between the inner cone and the outer cone, and
    detaching the collet with the at least one hair from the body of the extraction device for further manipulation.

10. The method of claim 8, wherein the step of closing the collet interspace is performed by pressing on the sliding arbor and pushing the sliding arbor in the forward direction.

\* \* \* \* \*